United States Patent [19]

Bender

[11] 4,303,074
[45] Dec. 1, 1981

[54] METHOD FOR APPLYING THERAPEUTIC HEAT

[75] Inventor: Joseph M. Bender, Winnipeg, Canada

[73] Assignee: Pascal & Associates, Ottawa, Canada

[21] Appl. No.: 47,581

[22] Filed: Jun. 11, 1979

Related U.S. Application Data

[62] Division of Ser. No. 893,764, Apr. 5, 1978, Pat. No. 4,186,294.

[30] Foreign Application Priority Data

Feb. 3, 1978 [CA] Canada .................................. 296254

[51] Int. Cl.³ .............................................. A61F 7/00
[52] U.S. Cl. .................... 128/399; 219/527; 219/528; 219/211; 219/347
[58] Field of Search ............... 219/211, 212, 217, 345, 219/347, 354, 527, 528, 529, 535, 543, 549; 128/379–389, 399, 402, 403, 411; 338/211, 212; 427/336, 376 R; 428/214, 408, 480

[56] References Cited

U.S. PATENT DOCUMENTS

| | | | |
|---|---|---|---|
| 2,299,162 | 10/1942 | Marick ................................ | 219/527 |
| 2,559,077 | 7/1951 | Johnson et al. ..................... | 219/543 |
| 2,769,892 | 11/1956 | Collins ................................ | 219/527 |
| 2,783,358 | 2/1957 | Wolf .................................... | 219/529 |
| 3,098,428 | 7/1963 | Dublirer et al. ..................... | 219/529 |
| 3,173,419 | 3/1965 | Dubilier et al. ..................... | 128/399 |
| 3,178,559 | 4/1965 | Fogel et al. ......................... | 219/527 |
| 3,621,192 | 11/1971 | Pohler ................................. | 219/527 X |
| 3,657,517 | 4/1972 | Hoyt .................................... | 219/528 X |
| 3,697,728 | 10/1972 | Stirzenbecker ..................... | 219/528 X |
| 3,710,075 | 1/1973 | Jablonowski ....................... | 219/211 |
| 3,751,620 | 8/1973 | Yuasa ................................. | 219/527 X |
| 3,865,656 | 2/1975 | Diener et al. ....................... | 428/408 |
| 3,900,654 | 8/1975 | Stinger ................................ | 428/214 |

*Primary Examiner*—Volodymyr Y. Mayewsky
*Attorney, Agent, or Firm*—Laff, Whitesel & Rockman

[57] ABSTRACT

A method for applying therapeutic heat by a therapeutic heating pad which is not hot to the touch provides substantial infrared radiation to a user. Accordingly it can be used for extended periods without feeling uncomfortable to the skin, while imparting deep therapeutic heat to the user. The heating pad is comprised of a radiant heat generating layer having a plane surface comprising means for radiating heat evenly from its surface, a pair of flexible electrically insulating and radiation permeable layers located adjacent and covering opposite sides of the layer, a thermal insulation layer disposed against and covering one of the electrically insulating layers, a radiation reflective layer disposed against and covering the outside surface of the thermal insulation layer, and a sealed radiation permeable envelope enclosing the entire heater. Preferably the flexible heat generating layer is comprised of a fiber glass mat impregnated with a resistive material, which material provides a surface temperature, when current is conducted therethrough, which is between 60 degrees Celsius and 65 degrees Celsius.

6 Claims, 4 Drawing Figures

METHOD FOR APPLYING THERAPEUTIC HEAT

This is a division of application Ser. No. 893,764 filed Apr. 5, 1978, now U.S. Pat. No. 4,186,294.

This invention relates to a novel form of heating pad which has been found to be useful for therapeutic heat application.

Certain types of painful conditions of the muscles or joints such as arthritic pain often have the application of heat prescribed to relieve the pain. Heat is normally applied in a variety of ways, for instance by the use of irritant rubbing compounds which cause local stimulation of blood vessels increasing body heat carried to the location, the use of infrared lamps, the use of radio frequency apparatus such as diathermy machines, the use of hot water bottles or electrically operated heating pads, etc.

While some or all of the aforenoted apparatus is alleged to work to some degree, all have certain disadvantages. For instance, the prolonged use of an infrared heating lamp can cause localized burning of the skin. Diathermy machines are specialized apparatus which require expensive skilled operators. Irritant rubs, while apparently generating local heat, sometimes irritate the skin. Hot water bottles maintain an uneven temperature with time, generally are applied too hot to the skin, and later cool to an ineffective temperature. They are thus uncomfortable for most of their time of application.

The present invention is directed to a novel form of electrically operated heating pad. Prior art heating pads are generally comprised of insulated electrical heating elements held within a sealed bag, covered with a washable removable cloth envelope. Such heating pads are resistance heated by the flow of electricity therethrough, which heat the surrounding insulated envelope. The pad is applied to an area of the body which is to be treated, and the hot pad provides fairly even heat to the skin.

However the use of this form of heating pad must be carefully controlled. Since the pad heats by conduction from the heating coils to the skin, it feels generally hot to the touch, and use must be limited or the skin can be burned, particularly if the user falls asleep on the pad. Due to the conduction of heat to the skin, the pad eventually begins feeling very uncomfortable. While such pads generally utilize thermostats to control the amount of heat generated, its use in a confined space, such as under the patient, generally causes the build up of heat on the skin which is conducted directly from the heating coils. The heat has been found to eventually become uncomfortable even at a generally low thermostatic setting.

The present invention is a therapeutic heating pad which operates using black body radiation of infrared heat, rather than conduction as in prior art pads. In the preferred embodiment the surface temperature of the pad exceeds the temperature of the human body, somewhat, but because of its unique design the heat is dissipated and it does not feel uncomfortably hot to the touch. It can, as a result be used for extended periods of time. Yet the radiant heat generated by the pad has been found to penetrate the tissues relatively deeply, thus providing an enhanced therapeutic effect. This is accomplished without the previously encountered hot or burning feeling on the skin.

The invention, in general, is a radiant therapeutic heater comprising a radiant heat generating layer having a plane surface comprising means for radiating heat evenly from its surface, a pair of flexible electrically insulating and radiation permeable layers located adjacent and covering opposite sides of the layer, a thermal insulation layer disposed against and covering one of the electrically insulating layers, a radiation reflective layer disposed against and covering the outside surface of the thermal insulation layer, and a sealed radiation permeable envelope enclosing the entire heater. The flexible heat generating layer is comprised of a fiber glass mat impregnated with a resistive material, which material provides a surface temperature, when current is conducted therethrough, which is between 60 degrees Celsius and 65 degrees Celsius.

A better understanding of the invention will be obtained by reference to the detailed description below, and to the following drawings, in which.

Figure 1:
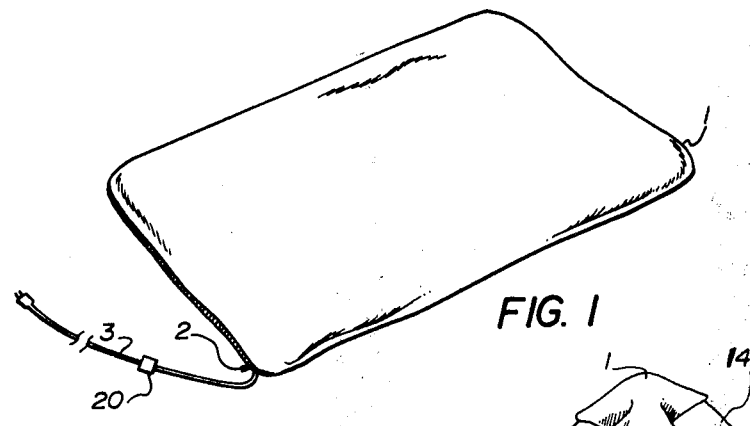
FIG. 1 is a perspective view of the complete heating pad.

Turning first to FIG. 1, the inventive heating pad is shown in perspective. The heating pad 1 preferably has a cloth cover of cotton or other natural fiber, formed into an envelope and closed by a zipper 2. A wire 3 extends from an opening which is closed by the zipper, for carrying current to the heating element which is controlled by an inline cord, on-off switch with indicator light 20. While a standard 117 volt AC mains plug is shown at the end of wire 3, it should be noted that upon appropriate design of the heating element, other potentials can be used, for instance 12 volts AC or DC, 75 volts AC or DC etc.

Figure 2:
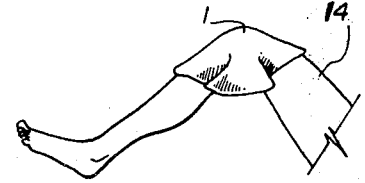
FIG. 2 is a side view of the heating pad in use.

FIG. 2 shows the heating pad 1 in use placed over the knee joint of the leg 14 of the user. As was noted earlier, the surface temperature of the pad is preferably 60 degrees Celsius to 65 degrees Celsius, and consequently the pad can be used in place for a long period of time with a comfortably hot feeling. Yet the infrared radiation appears to penetrate deeply into the body, thereby imparting maximum therapeutic effect by delivering deep heat without causing skin burns.

Figure 3:
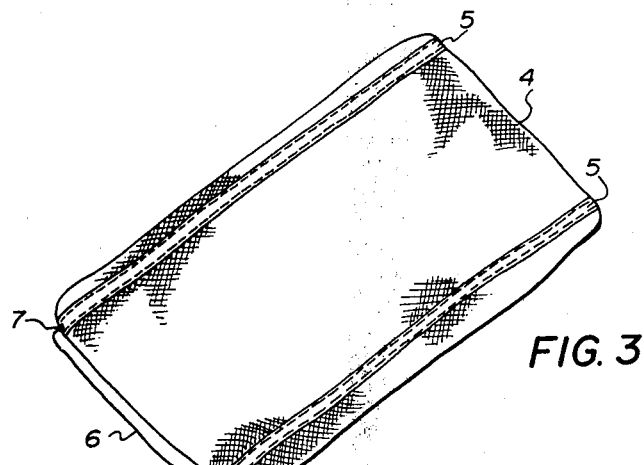
FIG. 3 is a plan view of the heat generating layer.

FIG. 3 shows the main heating element which is used within the heating pad 1. The heating element is comprised of a fiber glass mat or layer 4. The fiber glass mat is preferrably fabricated of woven clothlike Fiberglas. The material is throughly impregnated and saturated with a chemical compound which is a mixture of low and high resistance carbon to provide the required resistance. Saturation is carried out in such manner as to insure that the fiber glass is throughly covered inside and out homogeneously. Following saturation the material is passed through a series of steel rollers which remove the excess wet chemical, after which it is passed through an oven drying process and is finally subjected to heat of about 425 degrees Celsius to extract any remaining moisture in the material, thus stabilizing the carbon-graphite impregnated material.

The coating materials of the kind preferred to be used in the heating element of this invention is described in U.S. Pat. No. 3,865,626, issued Feb. 11, 1975.

Another mixture suitable for use with the fiber glass is comprised of the following:

45 parts graphite (83%–90%)
25 parts silicone
9 parts casein
20 parts probiofan L5

0.02–0.05 parts of silikorentschäumer

The quantity of the material impregnated in the fiber glass, which forms a resistive layer, ranges from about 0.1 grams per square meter to about 3 grams per square meter. After heat treatment, drawing and passing of the fiber glass through the rollers (the latter of which gauges the thickness of the particles of the impregnate adhereing to the material) sets the resistivity of the material.

It should be noted that other materials than fiber glass can be used as a base for the resistive material. For instance, as described in U.S. Pat. No. 3,865,626, a polyester film is treated with a solvent or swelling agent. Electroconductive particles, preferably carbon black is applied to the treated surface in a concentration corresponding to the desired resistance. The film is then subjected to heat treatment to solidify and retain the resistive material in the surface.

Conductive tapes 5, preferably of copper foil, are sewn into electrical contact with the resistance material along parallel edges of the fiber glass material. The tapes can be made of either woven or non woven material. A pair of wires 6 are then connected to the ends of the conductive tapes using clips 7.

It should be noted that as the resistivity of the material is measurable in ohms per square units, the material can be made in large sheets or rolls, and then cut to the required resistance. In the preferred embodiment, the heat element disipates 26.3 watts per square foot with an input voltage of 117 volts AC. The preferred dimensions for the heating pad element are 12 inches wide by 15 inches long. Depending on the specific design, however, the disipation can be made as low as 13 watts per square foot. However the pads or heaters can be made a variety of desired dimensions in length or width. Widths, for example, can range from 2 inches to 48 inches between copper conductor tapes.

It should be noted that since the resistance material is basically fabricated of carbon compound, the heating element is a black body radiator, which has a high efficiency of radiant heat dispersion which, it is believed, contributes to the effectiveness of the invention.

Figure 4:
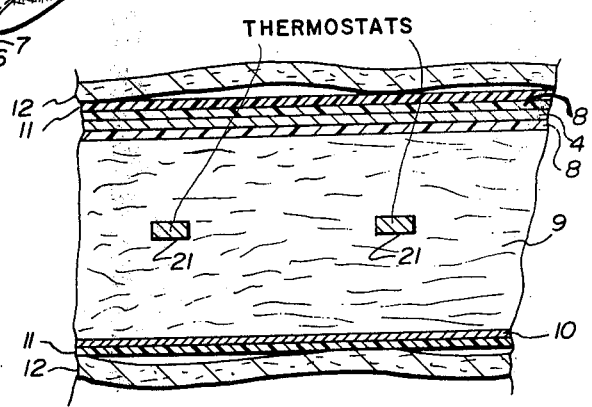
FIG. 4 is a crossectional view of the heating pad.

FIG. 4 shows a crossection of a portion of the complete heating pad. The heating element 4 has a pair of film isolator layers 8 covering its surfaces on its opposite sides. The isolator layers are insulative to electricity, but transparent to infrared radiation. The materials of the isolator layers are selected from the group comprising polyester, Teflon, Kapton type H300 and Kapton type F300 films, although the latter Kapton type film is preferred. A suitable thickness of film is 0.04 mil, which has been found suitable for the low temperatures produced.

Disposed against the outside of one of the isolator layers 8 is an insulating layer 9. The insulating layer is preferably spun glass of less than about 1 inch in thickness, but not thinner than $\frac{1}{4}$ inch thickness. Preferably the insulation is $\frac{1}{2}$ inch thickness.

A reflective layer 10 is disposed against the outer surface of the insulative layer 9. Preferably the reflective layer 10 is aluminum foil of about 0.02 mil thickness, polyester coated. However, other types of reflective materials could be used if highly heat reflective.

Current limiting control thermostats 21 are centrally located within the insulating layer 9 and distributed to sense whether any hot spots may be developing due to a fold, or the like in the pad. Connected in series with the heating element, they cut off power thereto in case the temperature becomes excessive. The thermostats are adherent to the insulating layer 9 preferably using 3M type #27 electrical Fibreglas* tape, tradename Kapton Tape.
*Trade Mark A sealed envelope comprising layers 11 encloses the entire heating pad. This envelope, which can be fabricated of vinyl, holds all of the above described layers in laminated position, and protects them against the intrusion of moisture or other contaminants. The pair of wires which contacts the conductive tapes, of course extend through a hole in the vinyl envelope, which hole is preferably sealed against the wires. Of course a sealed connector could be used with a detachable cord, if desired.

An outer cloth bag or envelope, shown as layers 12 encloses the vinyl envelope. Preferably the cloth bag is fabricated of terry towel, or other cotton or natural fiber material, which has been found to be most comfortable to the user. As noted above, the cloth bag can be closed by a zipper or with other fastening devices such Velcro closure or the like. The cloth bag may thus be removed and washed as desired.

In operation, the heating pad is plugged in or otherwise connected to a source of operating current. The heating pad is placed over a region to be therapeutically warmed with deep heat. Current passes through the resistance material of the fiber glass, creating a source of black body infrared radiation. The radiation is received by the body of the user, and appears to penetrate deeply. Yet the heating pad does not feel uncomfortably hot to the touch.

In the event the heating pad is heated before being applied to the user's body, should the heating pad have a resistivity which raises its temperature higher than that of the temperature of the human body, for instance to 140 degrees F., the pad may feel warm for an instant when it is applied to the body of the user. However it has been found that this warmth is almost instantly dissipated by the skin of the user, and further contact with the pad does not impart an uncomfortably hot sensation to the touch. Accordingly there is a very little heat conduction from the inventive structure, but there is substantial radiated heat. The radiated heat is received by receptive bodies opposite the side of the pad opposite the reflective layer. Yet the air which is in contact with the heating pad does not heat, since it is transparent to infrared radiated heat.

It has been found that the described structure radiates heat in the wave length band of between 9 and 12 microns, while the entire infrared bandwidth extends between 0.72 and 400 microns. It is believed that the particular bandwidth of the radiation which is emitted by this invention contributes to the apparent deep penetration and therapeutic effect obtained.

As noted earlier, the heating pad can be made of various sizes, such as the size given by example herein, blanket size, or of particular shape to match the shape of a portion of a users body.

Accordingly a heating pad has been invented which has significant advantages over prior art therapeutic heat applying devices. Such the pad gives its deep heat penetration by radiation, with a relatively low surface temperature, skin surface burns do not result from prolonged use. The pad is useable by the patient, and no specialist is required for its application. Nonconductive and virtually entire radiative infrared heat in the range of 9 to 12 microns is imparted to the user, which has been found to result in a penetrating deep heat, which patients have found to be highly successful in relief of symptoms of arthritic pain, etc.

It may now become evident to a person skilled in the art understanding this invention that other materials than the ones described can be substituted for the ones described, and that other embodiments and configurations may now be designed. All are considered within the scope and sphere of the invention, as defined in the appended claims.

The embodiments of the invention in which an exclusive property or privilege is claimed are defined as follows:

1. A method for applying therapeutic heat comprising the steps of:
   (a) generating radiant heat energy at a wavelength which penetrates into a human or animal body, said radiant heat being generated in at least one flexible electrically insulating and radiant energy permeable layer,
   (b) disposing a thermal insulation layer against the human or animal body and covering it with the layer forming the source of said radiant energy,
   (c) reflecting said radiant energy against the surface of and through the thermal insulation layer and into the human or animal body, and
   (d) sealing a radiant energy permeable envelope around the entire heater used in steps (a)-(c).

2. A method of applying radiant therapeutic heat as defined in claim 1 in which the radiant heat generated in step (a) is generated from a fiberglass mat impregnated with a resistive material.

3. The method of claim 2 wherein said fiberglass mat impregnation comprises:
   45 parts graphite (83%-90%),
   25 parts silicone,
   9 parts casein,
   20 parts probiofan L5,
   102-0.05 parts of silikorentschaumer.

4. A method of applying therapeutic heat comprising the steps of:
   (a) generating radiant heat energy at a wavelength which penetrates into a human or animal body, said radiant heat being generated in at least one flexible layer,
   (b) interposing an electrically insulating and radiant energy permeable layer between a human or animal body and the flexible layer, and
   (c) reflecting the radiant energy from the side of said layer opposite said body toward the body.

5. A method of applying radiant therapeutic heat as defined in claim 4 in which the radiant heat generated in step (a) is generated from a fiberglass mat impregnated with a resistive material.

6. The method of claim 5 wherein said fiberglass mat impregnation comprises:
   45 parts graphite (83%-90%),
   25 parts silicone,
   9 parts casein,
   20 parts probiofan L5,
   102-0.05 parts of silikorentschaumer.

* * * * *

UNITED STATES PATENT AND TRADEMARK OFFICE
CERTIFICATE OF CORRECTION

PATENT NO. : 4,303,074
DATED : December 1, 1981
INVENTOR(S) : J.M. BENDER

It is certified that error appears in the above—identified patent and that said Letters Patent is hereby corrected as shown below:

Please remove the name of the Assignee "PASCAL & ASSOCIATES" from the above-identified patent, as an Assignment was never issued or recorded in the application.

Signed and Sealed this

Twenty-first Day of September 1982

[SEAL]

Attest:

*Attesting Officer*

GERALD J. MOSSINGHOFF

*Commissioner of Patents and Trademarks*